United States Patent [19]
Dobbs et al.

[11] Patent Number: 5,487,098
[45] Date of Patent: Jan. 23, 1996

[54] MODULAR DETECTOR ARRANGEMENT FOR X-RAY TOMOGRAPHIC SYSTEM

[75] Inventors: John Dobbs, Hamilton; David Banks, Boxford, both of Mass.

[73] Assignee: Analogic Corporation, Peabody, Mass.

[21] Appl. No.: 447,181

[22] Filed: May 22, 1995

Related U.S. Application Data

[63] Continuation of Ser. No. 190,945, Feb. 3, 1994, abandoned.

[51] Int. Cl.⁶ ........................................................ A61B 6/02
[52] U.S. Cl. .................................................. 378/19; 378/4
[58] Field of Search ........................... 378/4, 19, 7, 145, 378/147, 149, 154; 250/370.09, 363.01, 363.02, 363.08

[56] References Cited

U.S. PATENT DOCUMENTS

| | | | |
|---|---|---|---|
| 4,306,155 | 12/1981 | Cotic | 378/19 X |
| 4,338,521 | 7/1982 | Shaw et al. | 250/370.09 |
| 4,414,473 | 11/1983 | Hoffman et al. | 378/19 X |
| 4,417,354 | 11/1983 | Pfeiler | 378/19 |
| 4,429,227 | 1/1984 | DiBianca et al. | 378/19 X |
| 4,934,832 | 6/1990 | Strauss | 378/4 X |
| 5,025,462 | 6/1991 | Saito et al. | 378/19 |
| 5,164,973 | 11/1992 | Takahashi et al. | 378/19 |

FOREIGN PATENT DOCUMENTS

| | | | |
|---|---|---|---|
| 2566176 | 12/1985 | France | 378/19 |
| 2940380 | 4/1981 | Germany | 378/19 |
| 0137656 | 10/1980 | Japan | 378/19 |

*Primary Examiner*—David P. Porta
*Attorney, Agent, or Firm*—Lappin & Kusmer

[57] ABSTRACT

Preassembled detector modules, each containing several detectors, and preassembled anti-scatter modules, each containing several anti-scatter plates, are mounted on a spine, which is attached to the rotating gantry of a CAT scanner by adjustable end supports. A pair of dowel pins in accurately drilled reference holes in the spine control the location and alignment of each module, one in a module round hole and one in a module slot. Critical dimensions in the modules are referenced to the hole, the slot, and reference surfaces on the modules contact the spine so as to reduce tolerance build-up. As such the modules can be easily manufactured using standard machine tools, and easily assembled and secured to a rotatable disk of a tomographic system.

41 Claims, 5 Drawing Sheets

MODULAR DETECTOR ARRANGEMENT FOR X-RAY TOMOGRAPHIC SYSTEM

RELATED APPLICATIONS

This is a continuation of application Ser. No. 08/190,945 filed on Feb. 3, 1994 now abandoned.

This application is related to co-pending U.S. patent application Ser. No. 08/191,428, filed in the name of Bernard M. Gordon; John Dobbs and David Banks contemporaneously herewith and assigned to the present assignee (Attorney's Docket Number ANA-44); and U.S. patent application Ser. No. 08/191,426, filed in the name of John Dobbs; David Banks and Leonhard Katz, contemporaneously herewith and assigned to the present assignee (Attorney's Docket Number ANA-47).

1. Field of the Invention

This invention relates generally to X-ray computer assisted tomography (CAT), and more particularly to tomographic detector systems.

2. Background of the Invention

Current CAT scanning equipment, is typically large, very heavily built and expensive. These attributes are at least partly responsible for its limited deployment, and therefore limited availability. Until now, however, these undesirable physical properties have been necessary because of the requirements of the CAT scan process.

CAT scanners of the third generation type include an X-ray source and X-ray detector system secured respectively on diametrically opposite sides of an annular-shaped disk. The latter is rotatably mounted within a gantry support so that during a scan the disk rotates about a rotation axis while X-rays pass from the source through an object positioned within the opening of the disk to the detector system.

The detector system typically includes an array of detectors disposed as a single row in the shape of an arc of a circle having a center of curvature at the point, referred to as the "focal spot," where the radiation emanates from the X-ray source. The X-ray source and array of detectors are all positioned so that the X-ray paths between the source and each detector all lie in the same plane (hereinafter the "slice plane," "rotation plane" or "scanning plane") normal to the rotation axis of the disk. Because the ray paths originate from substantially a point source and extend at different angles to the detectors, the ray paths resemble a fan, and thus the term "fan" beam is frequently used to describe all of the ray paths at any one instant of time. The X-rays that are detected by a single detector at a measuring instant during a scan is considered a "ray." The ray is partially attenuated by all the mass in its path so as to generate a single intensity measurement as a function of the attenuation, and thus the density of the mass in that path. Projections, i.e., the X-ray intensity measurements, are typically done at each of a plurality of angular positions of the disk.

An image reconstructed from data acquired at all of the projection angles during the scan will be a slice along the scanning plane through the object being scanned. In order to "reconstruct" a density image of the section or "slice" of the object in the defined rotation plane, the image is typically reconstructed in a pixel array, wherein each pixel in the array is attributed a value representative of the attenuation of all of the rays that pass through it during a scan. As the source and detectors rotate around the object, rays penetrate the object from different directions, or projection angles, passing through different combinations of pixel locations. The density distribution of the object in the slice plane is mathematically generated from these measurements, and the brightness value of each pixel is set to represent that distribution. The result is an array of pixels of differing values which represents a density image of the slice plane.

In order for the image reconstruction process to work, the position of the rays must be precisely known. It is well known to mount the detector array on the rotatable disk so that it is spatially offset with respect to the X-ray source within the scanning plane by an angle equivalent to one fourth of the spacing between the centers of adjacent detectors. With such an offset, the resulting second 180° measurements are taken at a displacement of one quarter detector spacing from those of the first 180° so that the second half rotation places rays at radii which are half way between the rays of the first half rotation. This makes ray placement even more critical.

In order to accurately position the rays without an unmanageable amount of calibration and correction, it is therefore very useful to have accurately located detectors, and measurements accurately timed so that the angular position of each detector for each projection is predetermined.

Further, since dense matter tends to scatter X-rays, it is important that any radiation that does not traverse a straight line from the source to each detector be excluded from the measurements by each such detector. To remove this scattered radiation, a series of very thin anti-scatter plates are typically inserted between the detectors and the object and aligned so as to collimate, or pass substantially only those rays traversing a straight, radial line between the source and each detector. Unfortunately, the need for the anti-scatter plates creates additional difficulties because if they cast an X-ray "shadow" on a detector, they will interfere with its measurements. Not only will the output of each shadowed detector be reduced, but it will also be modulated by the least vibration or lateral movement of the source, scatter plates and/or detectors.

The difficulty of meeting these requirements becomes evident when one considers that in order to provide the kind of resolution expected of modern X-ray tomographic scanners, the detectors number in the hundreds with several detectors located within a single degree of the fan beam arc. This makes the width of a typical detector on the order of a millimeter, and the dimensions of a typical anti-scatter plate about 38 mms long in the radial direction by about 0.1 mm thick, requiring extremely accurate detector and anti-scatter plate location and alignment. To further compound the problem, the whole assembly is usually rotated around the scanned object at a rate of about 15 to about 60 rpm, generating substantial varying forces and requiring ragged mounting techniques.

Previous attempts to satisfy these difficult requirements have resulted in machines of very large mass, requiring very costly, painstaking assembly techniques with a great deal of effort spent in anti-scatter plate and detector alignment. If for any reason one or more elements has to be replaced or realigned, the reassembly and realignment process is usually too demanding to be performed in the field, and the machine often has to be returned to the factor.

OBJECTS OF THE INVENTION

It is an object of the present invention to provide an improved X-ray tomographic detector system which provides the required location and alignment accuracy with greatly reduced assembly effort and relatively lower cost.

Another object of the present invention is to provide a tomographic detector system comprising component parts which can easily be replaced in the field.

And another object of the present invention is to provide a tomographic detector system in which the components are designed so that they can be easily manufactured with standard machine tools, which operate with extreme accuracy in accordance with rectangular coordinate systems, and yet assembled so as to provide extreme positional accuracy required by the polar coordinate system of a tomographic scanner.

Other objects of the present invention will in part be evident and will in part appear hereinafter. The invention accordingly comprises the apparatus possessing the construction, combination of elements, and arrangement of parts exemplified in the following detailed disclosure, and the scope of the application of which will be indicated in the claims.

SUMMARY OF THE INVENTION

In accordance with the present invention, the detector system includes a base support element in the form of a spine, a plurality of anti-scatter modules and a plurality of detector modules for attachment to the spine and means for mounting the spine to the rotation disk of the gantry. The spine preferably has a flat reference surface adapted to be positioned parallel to the scanning plane when the spine is properly attached to the rotation disk. The flat reference surface allows for the precise positioning of a plurality of reference holes. Each anti-scatter module and detector module has a flat reference surface adapted to contact the spine reference surface so as to fix the module relative to the spine reference plane (and therefore the scanning plane). Each module also preferably includes a round reference hole and a reference slot normal to the module reference surface for accurately positioning the module relative to the spine and each other. The anti-scatter module includes a plurality of anti-scatter plates accurately located and oriented with respect to the module reference hole, slot and reference surface. Each detector module includes a plurality of detectors accurately located and oriented with respect to the module reference hole, slot and reference surface. The reference holes and slots of the spine and each of the modules can be accurately positioned relative to the respective spine and module flat reference surface using the rectangular coordinate system of commercially available machine tools. The location of each anti-scatter module and each detector module on the spine is accurately determined by a dowel pin inserted through the round reference hole of the module and a spine reference hole provided in the spine reference surface, and the alignment of each anti-scatter module and each detector module is determined by a dowel pin in both its reference slot and a spine reference hole. For less tolerance build-up, the location of both an anti-scatter module and a detector module may be determined by a common dowel pin and spine reference hole, and each anti-scatter module may be located by a primary spine reference hole.

BRIEF DESCRIPTION OF THE DRAWINGS

For a fuller understanding of the nature and objects of the present invention, reference should be had to the following detailed description taken in connection with the accompanying drawings wherein.

DETAILED DESCRIPTION OF THE DRAWINGS

Figure 1:
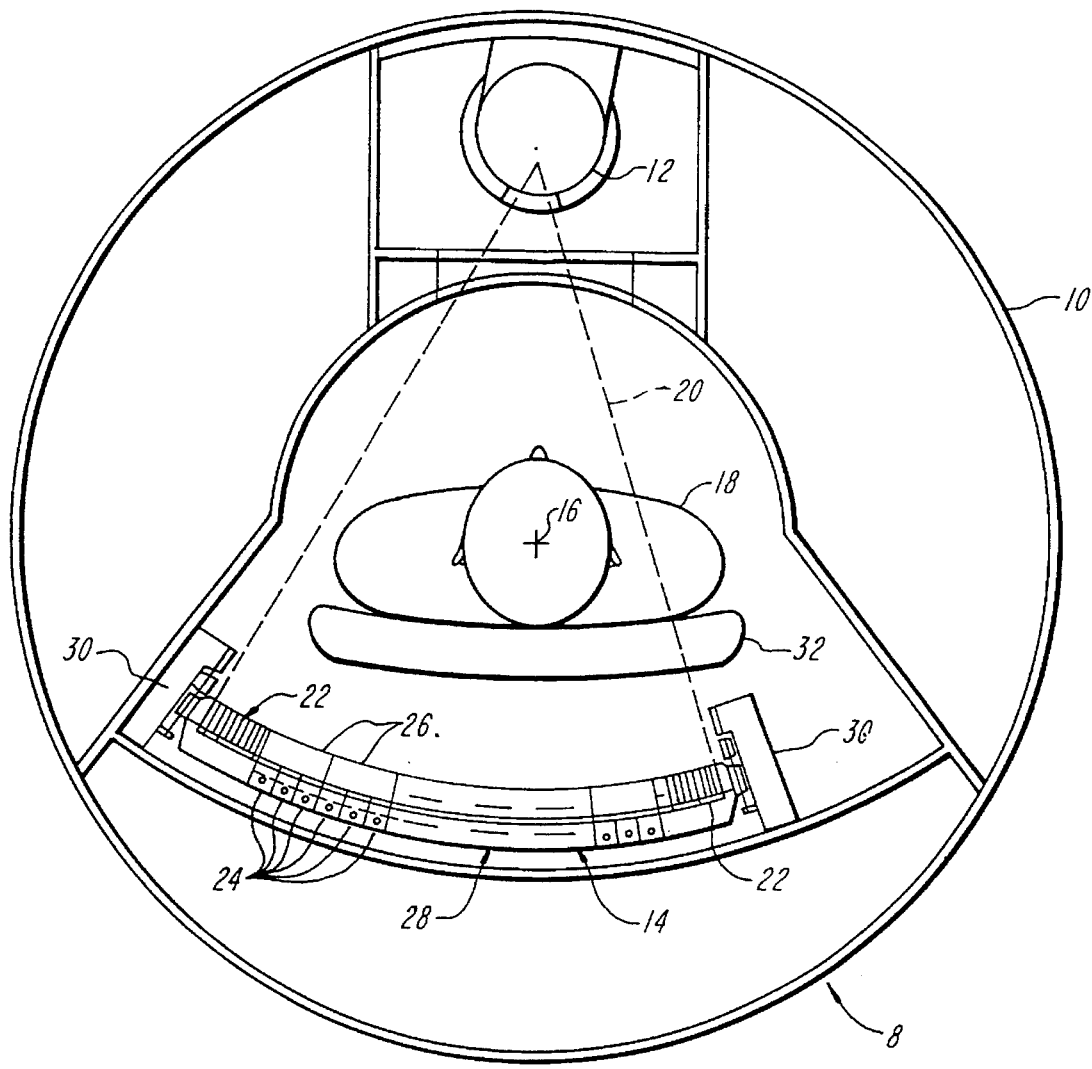
FIG. 1 is an axial view of a CAT scanner embodying the preferred arrangement of the present invention.

Referring to the drawings for a more complete understanding of the arrangement of the invention, FIG. 1 represents a CAT scanner 8 incorporating the principles of the invention. To provide the data for a CAT scan, scanner 8 includes a source 12 of X-rays and detector assembly 14 mounted to a disk 10. Source 12 and detector assembly 14 are rotated about rotation axis 16 (extending normal to the view shown in FIG. 1 ) so as to rotate around the object 18 that extends through the central opening of the disk during the CAT scan. Object 18 may be a part of a live human patient, such as the head or torso. Source 12 emits within the scanning plane (normal to rotation axis 16) a continuous fan-shaped beam 20 of X-rays, which are sensed by the detectors of assembly 14 after passing through object 18. An array of anti-scatter plates 22 is located between object 18 and the detectors of assembly 14 to substantially prevent scattered rays from being sensed by the detectors. In the preferred embodiment the detectors number 384 and cover an arc of 48°, although the number and angle can vary. Disk 10, which may advantageously be of a light weight material, such as aluminum, is caused to rotate rapidly and smoothly around axis 16. The disk 10 is of an open frame construction so that object 18 can be positioned through the opening of the disk. Object 18 may be supported, for example, on a pallet or table 32, which of course, should be as transparent as practical to x-rays. As disk 10 rotates, detectors of assembly 14 are periodically sampled to provide discrete measurements of x-rays passing in the scanning plane through object 18 from many projection angles. The measurements are then processed electronically with appropriate signal processing equipment (not shown), in accordance with well-known mathematical techniques, so as to produce the final image information. The image information may then be placed in memory, analyzed in a computer, or suitably displayed.

Prior to the present invention, great effort has been required to align each detector and the anti-scatter plates to insure proper placement of these components on the rotating disk of prior art tomography systems. It has occurred to us that one reason for the alignment difficulties is due to the fact that the arrangement of the detectors relative to the source is a polar coordinate problem with the center of the polar coordinates located at the focal spot of the X-ray source 12. On the other hand, machine tools for providing mounting holes in the disk commonly operates in a rectangular coordinate system.

In accordance with the present invention therefore the detector assembly is designed so that its components are easily made with standard machine tools operating in rectangular coordinate systems, and when assembled and secured to the disk 10 precisely align with the X-ray source in the polar coordinate system of the tomography system.

More specifically, referring again to FIG. 1, in accordance with the present invention the detector assembly 14 includes a base support element in the form of a supporting reference spine 28 provided with a flat datum or reference surface designed to be easily and precisely machined in the rectangular coordinate system of machine tools. The detectors and anti-scatter plates are each assembled into a plurality of identical modules 24 and 26, respectively, and the modules precisely machined also within the rectangular coordinates of standard machine tools. The modules are then accurately aligned and secured to the reference surface of the spine 28, and the spine supported by disk 10 with suitable supports, such as supports 30, so that the detectors all lie in the scanning plant: and subtend an equal angle with respect to the focal spot of the X-ray source 12.

Figure 2:
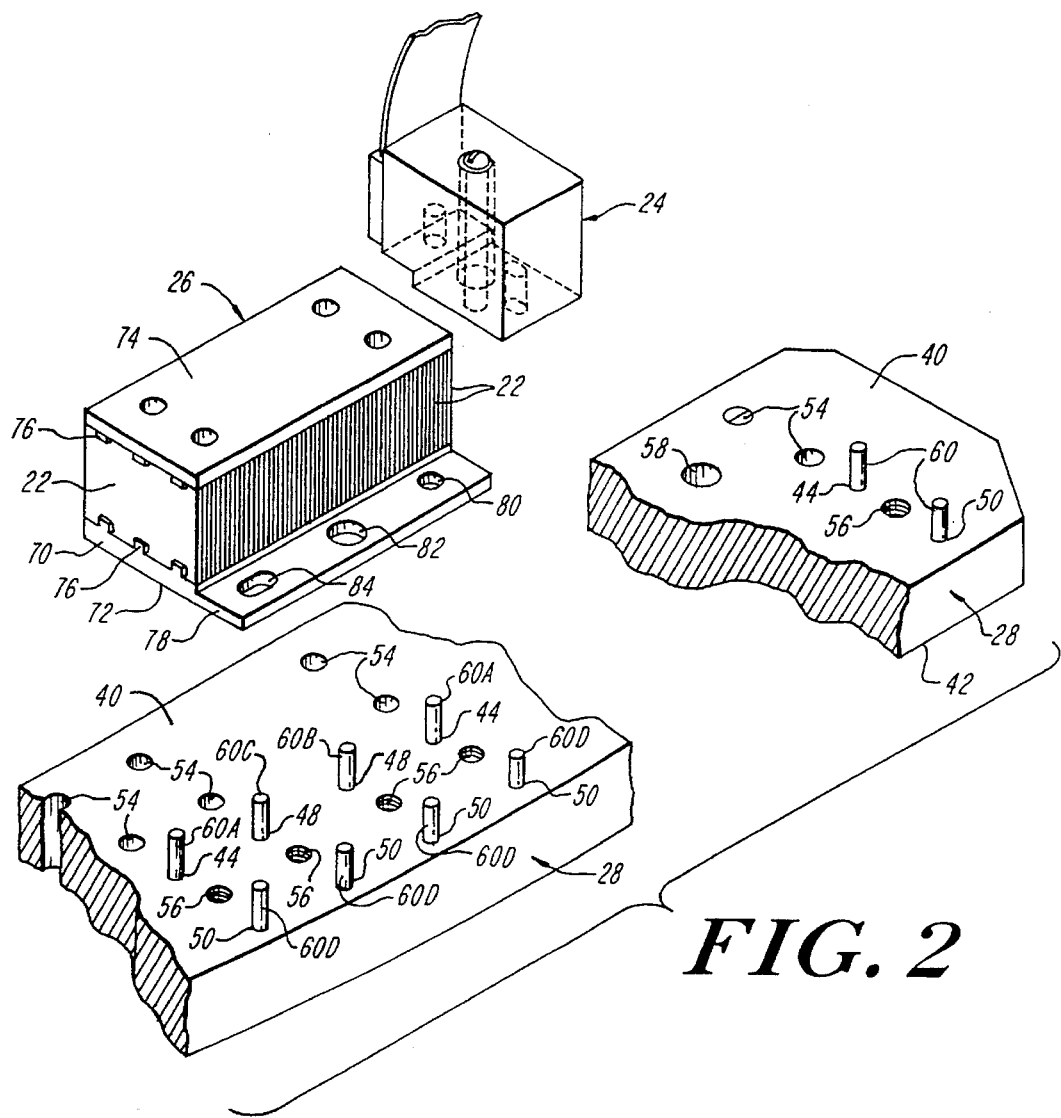
FIG. 2 is an exploded upper perspective view, partially cut away, illustrating the modular arrangement of the preferred embodiment of the detector system of the present invention.
Figure 3:
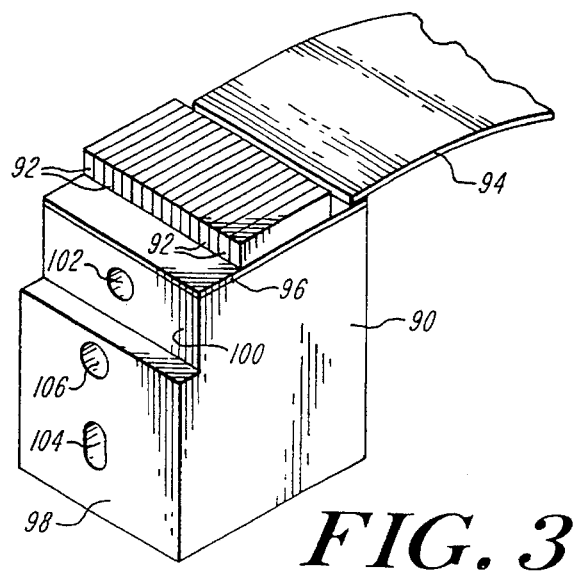
FIG. 3 is a lower perspective view of the preferred embodiment of the detector module made in accordance with the present invention.
Figure 5:
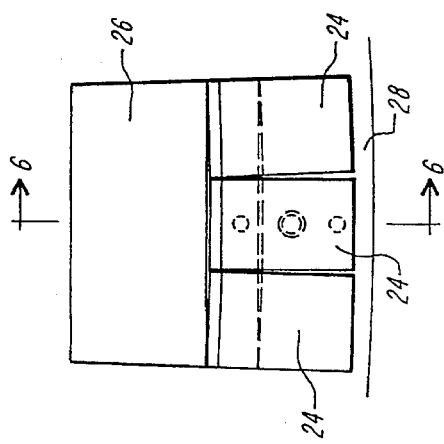
FIG. 5 is an axial view of three detector modules and an anti-scatter module attached to the spine of the preferred embodiment of the detector assembly.
Figure 6:
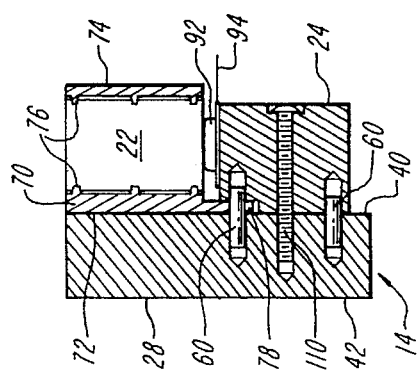
FIG. 6 is a tangential cross-sectional view taken along section line 6—6 in FIG. 5.
Figure 4:
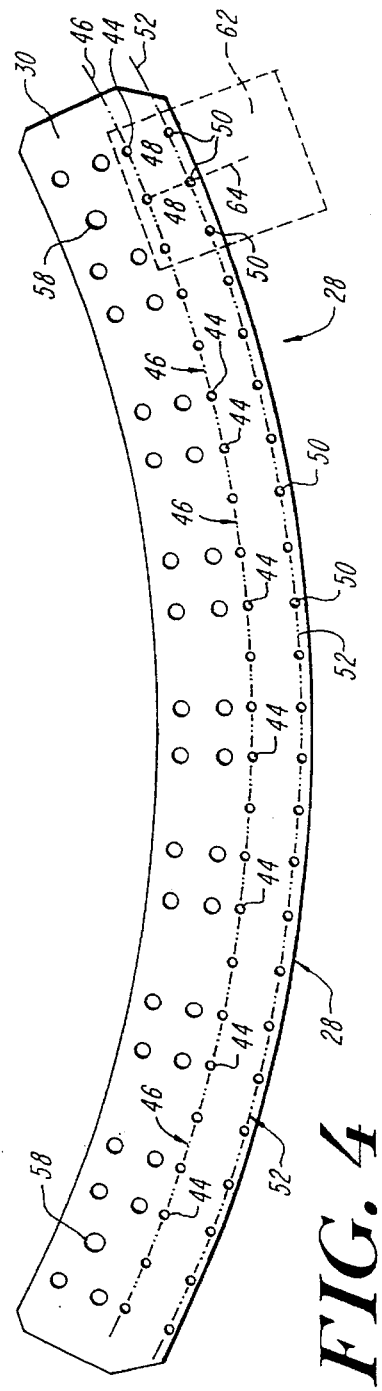
FIG. 4 is an axial view of the preferred embodiment of a spine for supporting the detector and anti-scatter modules in a fixed relationship, and for mounting the detector assembly to the gantry so that the modules are properly aligned with the scanning plane of the scanner.

An arrangement of the invention which facilitates the desired accurate location and alignment of the anti-scatter plates and detectors is illustrated in greater detail in FIGS. 2–12. Referring specifically to FIG. 2, the detector assembly 14 comprises spine 28, detector modules 24 and anti-scatter modules 26. In use, the complete detector assembly is secured to disk 10 and may include, for example, one spine, eight anti-scatter modules and 24 detector modules with each detector module supporting 16 detectors. The spine 28, a plan view of which is shown in FIG. 4, preferably is arc-shaped having a center of curvature coincident with the focal spot of the source 12 when properly secured to disk 10. As best seen in FIG. 6, the spine also includes two flat parallel surfaces 40 and 42, of which surface 40 may be considered a front, reference, or datum surface. These flat surfaces allow the very accurate drilling of reference holes into spine 28 from and normal to reference surface 40 using standard commercially available machine tools. As best seen in FIGS. 2 and 4, a series of primary reference holes 44, one for each anti-scatter module (and therefore 8 in number in the illustrated embodiment), is located on an arc 46 of predetermined curvature, which spaces them equally from x-ray source 12 when the spine is properly secured to disk 10, i.e., with the source at the center of curvature of the arc 46. The locations of holes 44 are accurately controlled with respect to the arc center and to each other. Associated with each primary reference hole 44 are two secondary reference holes 48, located on the same arc 46 and accurately located with respect to the primary reference holes. Also associated with each primary reference hole 44 are three additional secondary reference holes 50, located on an arc 52 concentric to that of the arc 46, accurately located with respect to each respective primary reference hole 44. In addition, as best seen in FIG. 2 associated with each primary reference hole 44 there may be mounting holes 54 and tapped blind mounting holes 56 (Seen in FIG. 2). A pair of through holes 58 (seen in FIG. 4) are useful to clamp spine 28 with respect to drilling equipment used for drilling all of the reference holes. A dowel pin 60 preferably is inserted in each reference hole 44, 48 and 50 of spine 28. All of the reference holes are sized for a slight interference fit with the dowel pins so that the pins will remain secure within the holes, while extending above the reference surface 40. Dowel pins 60 are therefore in accurate clusters of six (as illustrated by the dotted line box 62 in FIG. 4), three along arc 46, and three along arc 52 with one in each cluster in a primary reference hole 44. Preferably, each dowel pin along arc 46 will be paired with a dowel pin along arc 52 along a common radial line, such as line 64, passing through the center of curvature of the arcs 46 and 52.

For accurate positioning, anti-scatter plates 22 are first assembled into anti-scatter modules 26. An anti-scatter module 26 may include, for example, forty eight anti-scatter plates 22 mounted between a base plate 70, which as shown in FIGS. 2 and 6 has a flat external surface 72 considered as a reference surface, and a top plate 74. The mutually opposing surfaces of base plate 70 and top plate 74 preferably each includes means for supporting the plates 22 so that each plate will be radially aligned with the focal spot when the detector assembly is properly assembled and secured to the disk. The means preferably are very thin raised ridges 76, provided with positioning slots for receiving the respective anti-scatter plates 22. Base 70 is also formed with a lip 78 so as to provide room for positioning holes 80 and 82 and positioning slot 84. The centers of holes 80, 82 and slot 84 lie along an arc centered on the focal spot of the X-ray source, with the length dimension of the slot oriented along the line which extends from hole 80 and slot 84. The holes 80 and 82 and slot 84 are located so as to align respectively with a primary reference hole 44 and the two adjacent holes 48 of the spine so that the scatter plates will be properly positioned relative to the focal spot when the spine is secured to the disk. Hole 80 is sized to snugly receive a dowel pin 60A, and may be considered a primary reference hole. The narrower width of slot 84 is sized to snugly receive a dowel pin 60C so as to tightly position the anti-scatter module along the radial lines that extend to the focal spot, but the elongated length of the slot allows for tolerances in the spacing between the two dowel pins. The center hole 82 is oversized to accommodate without touching the third center dowel pin 60B positioned in the secondary reference hole 48 along the arc 46. The base plate 70 and plate 74 may be of aluminum for stability, low mass and high thermal conductivity, although other materials can be used. Anti-scatter plates 22 are commonly of tungsten, although other materials may be used, and can be made from stock materials.

The preferred detector module 24 is shown in further detail in FIG. 3. This module comprises a metal block 90 with an array of solid state detectors 92 and a multi-conductor ribbon cable 94, or other flexible connection, mounted on one face thereof. Block 90 may also advantageously be of extruded aluminum, although other materials can be used. Detectors 92 may each comprise a scintillating crystal to convert x-ray energy into light and a photo-diode to convert the light to electric current. The diodes may be formed by well known techniques on a substrate 96 and the crystals cemented directly on top of the diodes. Multi-conductor ribbon 94 may be attached by solder or otherwise to substrate 96 so that the output of each detector is individually fed through a corresponding conductor in the ribbon to the scanner signal processing components. The completed substrate assembly may be cemented onto block 90. Module 24 may contain, for example, 16 detectors. If they are mounted at ⅛ degree arc intervals, their centers will be less than two millimeters apart. Uniformity of detector spacing, as previously mentioned, is important for the assignment of measurements to the correct pixels in the reconstructed image. While uniformity of detector characteristics is desirable, in practice each detector is preferably calibrated over the range of anticipated temperatures. Good thermal bonding for uniform detector temperature, therefore is desirable.

Block 90 has a flat surface 98 for mounting against spine surface 40. Surface 98 may be considered a reference surface. A section of the block near the detectors is recessed to form another flat surface 100 parallel to surface 98. The amount of recess exceeds the thickness of lip 78 of module 26, so that surface 100 will clear the top of the lip when both surfaces 98 and 72 of the detector module and anti-scatter module respectively are against reference surface 40 of spine 28. For accurate location of detector module 24, a round reference hole 102 is positioned in and normal to surface 100 and is sized to tightly receive a dowel pin 60A, 60B or 60C positioned in the spine 28 and extending through a respective hole 80, 82 or slot 84 of the lip 78. The length dimension of a reference slot 104 in surface 98 is located on a line with hole 102 that is perpendicular to the array of detectors. The width of the slot 104, in the direction parallel to the detector array, is dimensioned to provide a snug fit over a dowel pin 60D, but provides clearance in its length direction so as to accommodate tolerances in the spacing between the respective pin 60A, 60B, or 60C to which the pin 60D is paired. A hole 106 through block 90 is located and sized to accept a mounting bolt 110 (see FIG. 6) and oversized relative to the tapped blind mounting hole 56 so as to accommodate any tolerances between the holes 48, 56 and 50 of spine 28 along the radial line to which the detector is fixed. Detectors 92 are very accurately positioned with respect to reference hole 102 and reference slot 104.

When the arrangement of the invention is assembled as indicated in FIG. 2, flat surface 72 of each anti-scatter module 26 and flat surface 98 of each detector module 24 rest against spine reference surface 40. Each anti-scatter module is located by the dowel pin 60A that extends through its reference hole 80 into a primary reference hole 44 and aligned by the dowel pin 60C that extends through its reference slot 84 into a spine reference hole 48. The dowel pin 60B that extends through enlarged hole 82 does not touch module 26. Each detector module 24 is located by a dowel pin 60A, 60B or 60C that extends from its respective reference hole 102 through a hole in lip 78 of an anti-scatter module 26 into a respective reference hole 44 or 48 in spine 28. It is likewise aligned by a dowel pin 60D that extends from its reference slot 104 into a reference hole 50 in spine 28. A bolt 110 through detector module hole 106 into a threaded hole 56 of spine 28 fastens each module 24 securely to spine 28, while anti-scatter modules are secured by four bolts (not shown) to the spine. This modular assembly is shown in the FIGS. 5 and 6.

In this arrangement, according to the invention, the goal of placing the detectors uniformly apart and equidistant from the x-ray source and lining up the anti-scatter plates to fall between and not shadow the detectors is met by a combination of factors: first, instead of positioning; the mounting holes radially into the mounting structure of the disk as in the prior art, an arc shaped spine is provided with flat surfaces perpendicular to the axis of the arc. This provides a datum plane into which holes parallel to the axis of this arc, may be provided. These flat surfaces enable much more accurate location of reference holes.

Second, each module is held at its proper position by two pins inserted into the drilled reference holes. Only one pin, however, goes into a round hole in the module; the other is in a slot that is elongated in line with the round hole.

Finally, the same pins that position an anti-scatter module also locate two of the three associated detector modules. The associated detectors and anti-scatter plates are therefore keyed to the same primary reference location, and every anti-scatter module is keyed to a primary reference hole in the spine. The accuracy of the drilled reference holes, therefore, is transferred to the module placement without accumulated tolerances. The result is that the accuracy with which the individual modules are manufactured is diminished minimally in assembling the eight anti-scatter modules and 24 detector modules on the spine. Field replacement of one or more modules therefore, is enabled without the need to realign the whole array. Finally, both modules 24 and 26 are easily made from stock materials with the placement of the anti-scatter plates and holes easily accomplished using the rectangular coordinate system of standard machine tools.

Figure 7:
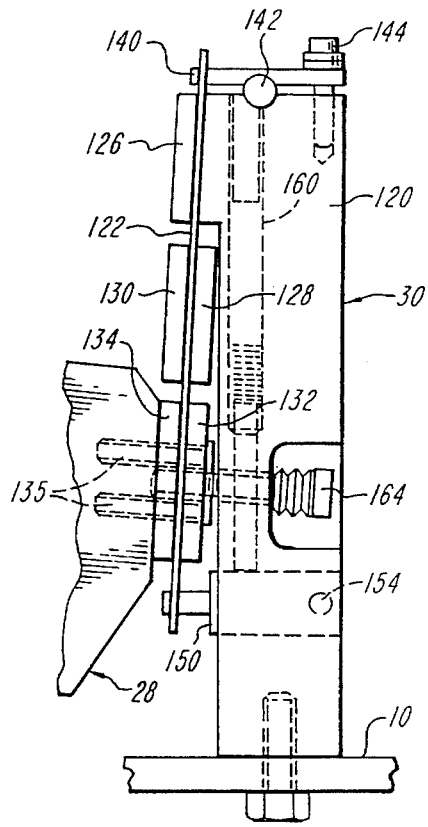
FIG. 7 is an axial view of the post support for attaching the spine to the rotating disk.
Figure 9:
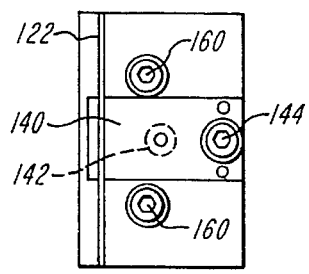
FIG. 9 is a radial view of the post support shown in FIGS. 7 and 8.
Figure 11:
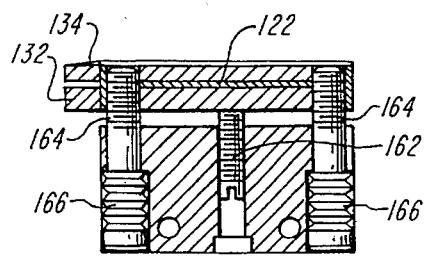
FIG. 11 is an approximate, radial cross section taken through line 11—11 of FIG. 10.
Figure 12:
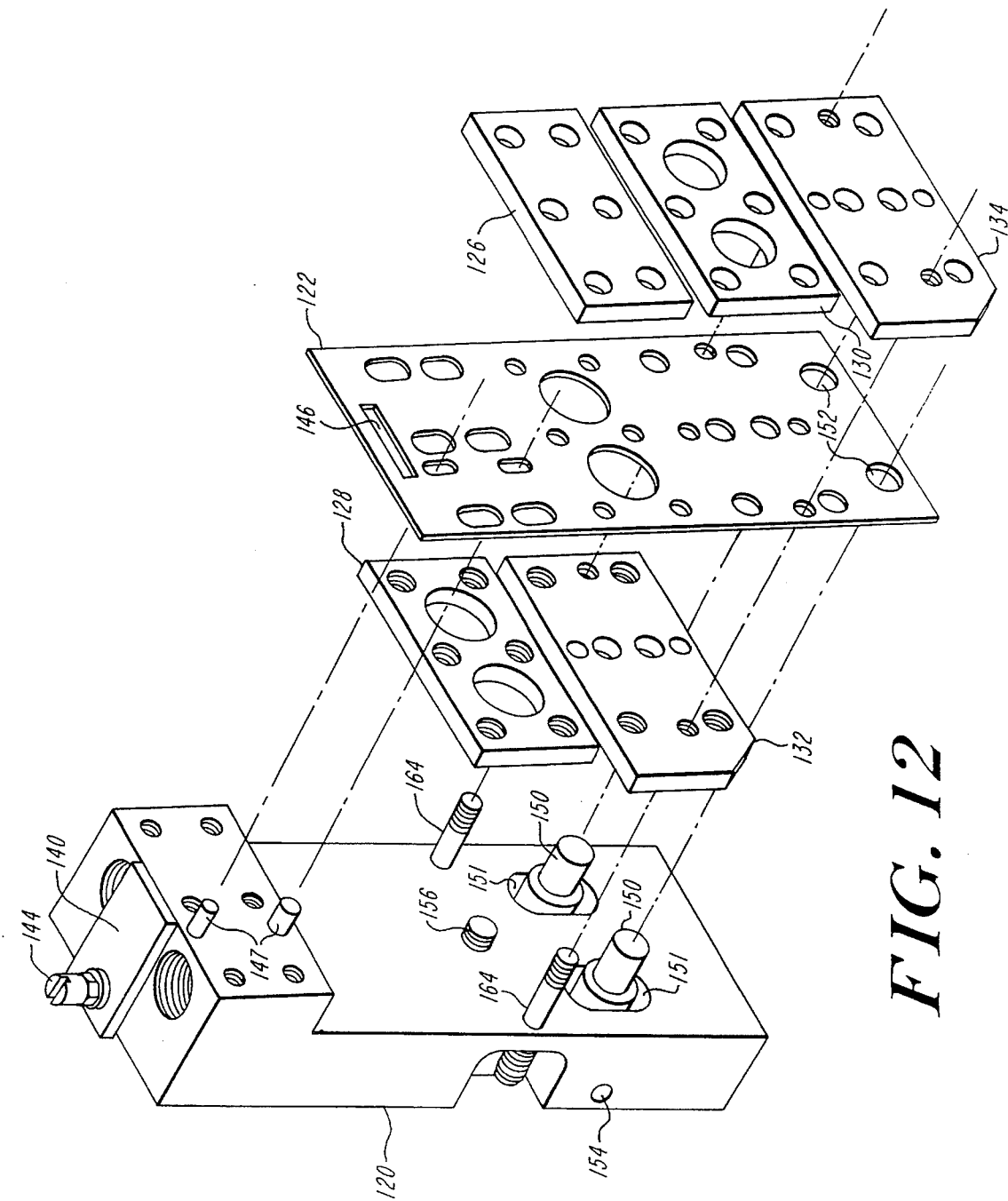
FIG. 12 is a partially exploded perspective view of the support shown of FIGS. 7–11.

A suitable arrangement for supports 30 to attach each end of spine 28 to disk 10 is shown in FIGS. 7–11, and the partially exploded assembly drawing of FIG. 12. The end of support 30 nearest the x-ray source is shown as the top in these drawings. The major components of a support 30 are a support body 120, which as seen in FIG. 7 bolts to disk 10, a thin, flexible mounting plate 122, which bolts at opposite ends to body 120 and spine 28.

Figure 8:
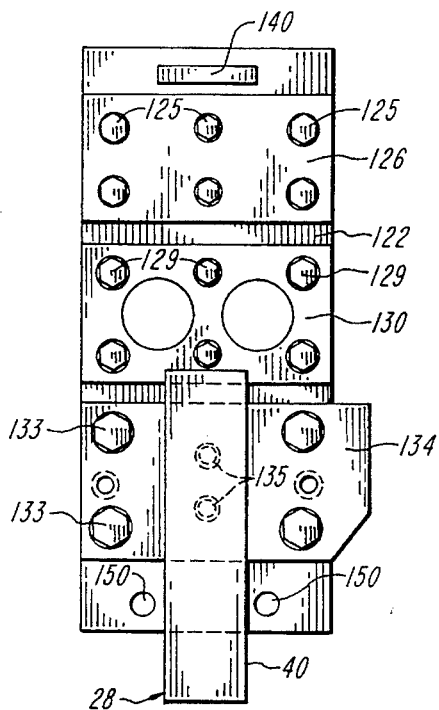
FIG. 8 is a tangential side view of the post support shown in FIG. 7.

For reasons described in copending application, U.S. Ser. No. 08/191,428, filed in the name of Bernard M. Gordon; John Dobbs and David Banks contemporaneously herewith and assigned to the present assignee (Attorney's Docket Number ANA-44), flexible plate 122 is sandwiched between three pairs of rigid surfaces, five of which are on separate stiffeners 126, 128, 130, 132 and 134. As best seen in FIG. 8, a first stiffener 126 holds the upper section of plate 122 against body 120 by bolts 125. A pair of stiffeners 128 and 130 may be applied to opposite sides of the middle section of plate 122 by bolts 129 through stiffener 128 and plate 122 into stiffener 130. Similarly, a pair of stiffeners 132 and 134 may be secured to opposite sides of a lower section of plate 122 by bolts 133. As best seen in FIGS. 7 and 8 additional bolts 135 through the center of stiffeners 132 and 134 and plate 122 into threaded holes in the end of spine 28 securely fasten the spine 28 to stiffening member 134, and thus to support 30.

As best seen in FIGS. 7 and 12, fine adjustment of the position of spine 28 in the radial direction, toward anti away from the source 12, to assure that all detectors are the same distance from the focal spot, may be provided by a lever 140, a pivot ball 142, a screw 144, located at the top of each support 120. One end of lever 140 protrudes through a rectangular hole 146 (See FIG. 12) in plate 122. Screw 144 extends through lever 140 at the other end and is threaded into the top of body 120. Ball 142, partly recessed into body 120 and into lever 140, serves as a fulcrum so that as screw 144 is driven into body 120, plate 122 is raised, and vice versa. The elongated holes 148 in plate 122 through which bolts 125 extend accommodate this adjustment, which is made before stiffener 122 is firmly secured. A pair of dowel pins 147, in body 120, and associated slots 149 in plate 122 and stiffener 126, assure radial alignment wherein the width of each slot is dimensioned to tightly receive the corresponding pin.

Figure 10:
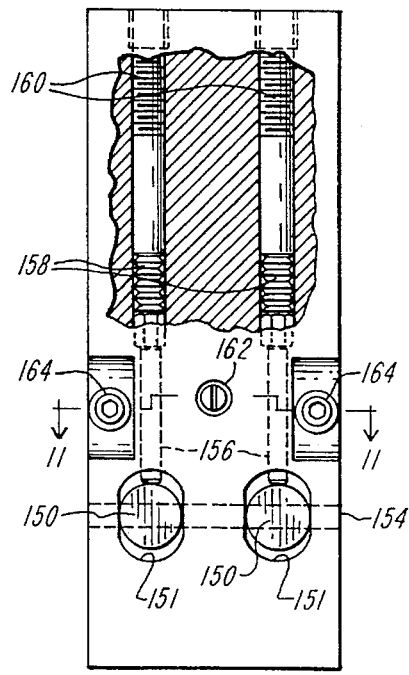
FIG. 10 is a partial tangential view of the post support shown in FIGS. 7–9.

Plate 122 may be kept under constant tension to avoid movement when subjected to operating forces by a pair of tensioning levers 150, which protrude through slots 151 provided in body 121, and into holes 152 in plate 122. Both levers 150 pivot up and down in slots on a common pivot rod 154, that passes through body 120 and levers 150. As best seen in FIG. 10, driving each of tensioning levers 150 may be a push rod 156, an appropriate stack of compression washers 158 and a tensioning screw 160. The compression washers maintain a constant pressure on push rods 156 and therefore constant tension on plate 122 over a limited range of movement. The size washer is chosen according to the amount of tension desired, and the number of washers in the stack is chosen to accommodate the range of movement desired for final adjustment.

Finally, to provide the very fine tangential adjustment of spine 28 and therefore the detector assembly, adjustment bolt 162 in a threaded hole along the center line of body 120 pushes against stiffener 132. To stabilize the position of stiffener 132, a pair of tensioning bolts 164 (see FIGS. 7 and 10) are threaded into stiffeners 132 and 134. A stack of compression washers 166 on each bolt 164 between its head and body 120 serves to keep the position of spine 28 as adjusted by bolt 162 under constant tension throughout its micro adjustment range. Supports 30, therefore, provide rugged, firm positioning for spine 28 with the needed adjustment capability.

We have thus described a modular arrangement for a detector assembly for a tomography system, such that the arrangement provides accurate location and alignment of detectors and anti-scatter plates at reduced manufacturing and assembly cost, and which supports easy field replacement of both. While only one such arrangement has been illustrated, other arrangements will occur to those skilled in the art which do no depart from the spirit and scope of the invention as set forth in the claims that follow.

Since certain changes may be made in the above apparatus without departing from the scope of the invention herein involved, it is intended that all matter contained in the above description or shown in the accompanying drawings shall be interpreted in an illustrative and not in a limiting sense.

What is claimed is:

1. A modular arrangement for X-ray detector assembly for use with a source of X-rays in a X-ray system, said arrangement comprising:

at least one detector module, said detector module including a reference surface and one or more detectors, fixed relative to said reference surface, for detecting X-rays generated by said source;

at least one anti-scatter module, said anti-scatter module including a second reference surface and means, fixed relative to said second reference surface, for reducing the amount of scattered X-rays that are received by said detector; and base support means, adapted to be secured to said X-ray system, for supporting said detector and anti-scatter modules and having a base reference surface and including positioning means for properly positioning and fixing each of said modules to said base support means and with respect to each other;

wherein said positioning means comprises three pins extending through said base reference surface and fixed relative to said base support means such that a first of said pins cooperates with said detector module, the second of said pins cooperates with said anti-scatter module and the third of said pins cooperates with and is common with respect to both said detector and anti-scatter modules so that the reference surfaces of each of said modules is in mutually confronting relationship with the base reference surface and so that the detector module and anti-scatter module are accurately positioned with respect to one another and to said source when said modules and base support means are secured to said X-ray system.

2. The arrangement of claim 1, wherein each of said reference surfaces is flat.

3. The arrangement of claim 1, wherein each of said detector and anti-scatter modules includes (a) one circular hole for tightly receiving the third of said pins and (b) a slot having a width which is narrower than its length, and wherein the length of said slot is aligned with said one hole, the width of the slots of said modules are dimensioned to tightly receive the respective first and second of said pins while the length of the slots of said modules accommodates tolerances between said first and third of said pins and between the second and third of said pins.

4. The arrangement of claim 1, wherein one of said modules includes a lip for extending its reference surface and the other of said modules includes a recess for receiving said lip so that the reference surfaces of said modules are coplanar and in contact with the reference surface of said base support means when said modules are fixed to said base support means by said positioning means.

5. The arrangement of claim 4, wherein said first and third of said pins are substantially aligned with said source when said modules and base support means are secured to said X-ray system, and said second and third of said pins are disposed along an arc having a center of curvature at said source when said modules and base support means are secured to said X-ray system.

6. The arrangement of claim 1, wherein said arrangement includes a plurality of detector modules and a plurality of anti-scatter modules.

7. The arrangement of claim 6, wherein said positioning means includes two pins for positioning each of said modules relative to said base support means, and wherein two of said detector modules respectively share the two pins used for supporting a corresponding one said anti-scatter modules.

8. The arrangement of claim 7, further including attachment means for securing said base support means to said X-ray system.

9. The arrangement of claim 8, wherein said attachment means includes means for adjusting the position of said base support means relative to said source.

10. A modular arrangement for a X-ray detector assembly for use with a source of X-rays in an X-ray system, said arrangement comprising:

at least one detector module, said detector module including a reference surface and one or more detectors, fixed relative to said reference surface, for detecting X-rays generated by said source;

at least one anti-scatter module, said anti-scatter module including a second reference surface and means, fixed relative to said second reference surface, for reducing the amount of scattered X-rays that are received by said detector;

base support means, adapted to be secured to said X-ray system, for supporting said detector and anti-scatter modules and having a base reference surface and including positioning means for properly positioning and fixing each of said modules to said base support means so that the reference surfaces of each of said modules are in mutually confronting relationship with the base reference surface and so that the detector module and anti-scatter module are accurately positioned with respect to said source when said modules and base support means are secured to said X-ray system; and further wherein one of said modules includes a lip for extending its reference surface and the other of said modules includes a recess for receiving said lip so that the reference surfaces of said modules are coplanar and in contact with the reference surface of said base support means when said modules are fixed to said base support means by said positioning means.

11. The arrangement of claim 10, wherein said arrangement includes a plurality of detector modules and a plurality of anti-scatter modules.

12. The arrangement of claim 11, wherein said base positioning means comprises at least two primary pins for positioning each of said modules relative to said base support means, and wherein at least some adjacent detector modules respectively share two adjacent pins also used for supporting an associated anti-scatter module.

13. A modular arrangement for an X-ray detector assembly carried opposite a source of X-rays on a rotating disk of a tomographic system, said arrangement comprising:

(A) a spine having a substantially flat reference surface and a plurality of spine reference holes in and substantially normal to said spine reference surface;

(B) a plurality of anti-scatter modules for attachment to said spine, each anti-scatter module having:
(a) means defining a substantially flat anti-scatter module reference surface for contacting said spine reference surface;
(b) a round, anti-scatter module reference hole normal to said anti-scatter module reference surface;
(c) an anti-scatter module reference slot normal to said anti-scatter module reference surface and having its elongated dimension in line with said round reference hole, said anti-scatter module round hole and reference slot also lying along an arc of a circle whose center is said source of X-rays; and
(d) a plurality of anti-scatter plates, accurately located and oriented with respect to said anti-scatter module reference hole, reference slot and reference surface;

(C) a plurality of detector modules for attachment to said spine, each detector module having:
(a) means defining a substantially flat detector module reference surface for contacting said spine reference surface;
(b) a round detector module reference hole normal to said detector module reference surface;
(c) a detector module reference slot normal to said detector module reference surface, said detector module reference slot having its elongated dimension in line with said round detector module reference hole; and
(d) a plurality of x-ray detectors, accurately located and oriented with respect to said detector module reference hole, reference slot and reference surface;

(D) spine mounting means for mounting said spine to said tomographic system;

(E) a plurality of dowel pins;

(F) the location on said spine reference surface of each of said anti-scatter and detector modules being determined by one of said dowel pins respectively in each of its respective round reference hole and a spine reference hole; and (G) the alignment of each of said anti-scatter and detector modules being determined by one of said dowel pins respectively in each of its respective reference slot and a spine reference hole.

14. An arrangement as in claim 13, wherein the locations of both an anti-scatter module and a first detector module are determined by the same dowel pin and spine reference hole.

15. An arrangement as in claim 14, wherein said plurality of spine reference holes comprises:

a first plurality of primary reference holes, accurately located with respect to each other; and a second plurality of secondary reference holes associated with and accurately located with respect to each respective reference hole, the location of each of said anti-scatter modules being determined by one of said dowel pins in a primary reference hole; and the alignment of each of said anti-scatter modules being determined by one of said dowel pins in a secondary reference hole.

16. An arrangement as in claim 14, wherein the dowel pin and spine reference hole that determine the location of a second detector module also determine the location of an anti-scatter module in alignment with said first and second detector modules.

17. An arrangement as in claim 16, wherein the dowel pin that determines the location of a third detector module, that is positioned between said first and second detector modules, passes through without touching an oversized anti-scatter module reference hole normal to said anti-scatter module reference surface.

18. An arrangement as in claim 17, wherein there are more of said detector modules than said anti-scatter modules.

19. An arrangement as in claim 13, wherein said mounting means attaches to opposite ends of said spine and to said disk of said tomographic system.

20. An arrangement as in claim 19, wherein said mounting means comprises first adjusting means for making fine adjustments in the distance between each of said spine ends and said x-ray source.

21. An arrangement as in claim 19, wherein said mounting means comprises second adjusting means for making fine adjustments in the angular rotation of said spine with respect to said x-ray source.

22. A modular arrangement for an X-ray detector assembly carried opposite a source of X-rays on a rotating disk of a tomographic system, said arrangement comprising:

(A) a spine having a substantially flat reference surface and a plurality of spine reference holes in and normal to said spine reference surface;

(B) a plurality of anti-scatter modules for attachment to said spine, each anti-scatter module having:
(a) means defining a substantially flat reference surface for contacting said spine reference surface;
(b) a round reference hole normal to said anti-scatter module reference surface;
(c) a reference slot normal to said anti-scatter module reference surface and having its elongated dimension in line with said round reference hole; and
(d) a plurality of anti-scatter plates, accurately located and oriented with respect to said anti-scatter module reference hole, reference slot and reference surface;

(C) a plurality of detector modules, greater than the number of said anti-scatter modules, for attachment to said spine, each detector module having:

(a) means defining a substantially flat reference surface for contacting said spine reference surface;
(b) a round reference hole normal to said detector module reference surface;
(c) a reference slot normal to said detector module reference surface, said detector module reference slot having its elongated dimension in line with said detector module round reference hole; and
(d) a plurality of X-ray detectors, accurately located and oriented with respect to said detector module reference hole, reference slot and reference surface;

(D) spine mounting means for mounting said spine to said tomographic system;

(E) a plurality of dowel pins;

(F) the location on said spine reference surface of each of said anti-scatter and detector modules being determined by one of said dowel pins respectively in each of its respective round reference hole and a spine reference hole; and (G) the alignment of each of said anti-scatter and detector modules being determined by one of said dowel pins respectively in each of its respective reference slot and a spine reference hole.

23. In a modular arrangement for an X-ray detector assembly for use with a source of X-rays in an X-ray system wherein at least one detector module and at least one anti-scatter module are mounted in alignment on a substantially flat base reference surface of a base support means adapted to be secured to said X-ray system for supporting said detector and anti-scatter modules, the improvement comprising:

(a) each said detector module comprising a substantially flat detector reference surface parallel to and in contact with said base reference surface, and at least first and second detector module positioning: means aligned within a plane passing through said source of X-rays;

(b) each said anti-scatter module comprising a substantially flat anti-scatter reference surface parallel to and in contact with said base reference surface, and at least first and second anti-scatter module positioning means lying along an arc of a circle whose center is coincident with said source of X-rays;

(c) said base reference surface comprising base positioning means adapted to align and mate respectively with said detector module positioning means and said anti-scatter module positioning means for properly positioning and fixing each of said modules to said base support means so that the reference surface of each of said modules is in mutually confronting relationship with the base reference surface and so that the detector module and anti-scatter module are accurately positioned with respect to said source when said modules and base support means are secured to said X-ray system; and, (d) fastening means for securing said detector and anti-scatter modules to said base support means.

24. An arrangement according to claim 23, wherein said first and second detector module positioning means respectively includes first and second detector module positioning openings extending substantially normal to said detector reference surface and aligned within said plane, said first and second anti-scatter module positioning means respectively includes first and second anti-scatter module positioning openings extending substantially normal to said anti-scatter reference surface and disposed on said arc of said circle, said base support positioning means includes base support positioning openings extending normal to said base reference surface, said arrangement further comprising pins for insertion in said openings so that detector modules and anti-scatter modules are accurately positioned with respect to each other and to said source when said modules and base support means are secured to said X-ray system.

25. An arrangement according to claim 24, wherein each said detector module is adapted to cooperate with an anti-scatter module so that one of said detector module positioning openings is aligned with one of said anti-scatter module positioning openings so as to receive a common one of said pins.

26. An arrangement of claim 25, wherein said openings of each of said modules comprises a first, circular hole for tightly receiving said common pin and a slot having a width which is narrower than its length, and wherein the length of said slot is aligned with said first, circular hole, the width of the slot is dimensioned to tightly receive corresponding second and third ones of said pins, while the length of the slot accommodates tolerances between said common pin and the corresponding second and third ones of said pins.

27. A modular arrangement for X-ray detector assembly for use with a source of X-rays in an X-ray system, said arrangement comprising:

at least one anti-scatter module, said anti-scatter module including a first reference surface and means, fixed relative to said first reference surface, for reducing the amount of scattered X-rays emerging from said anti-scatter module;

a plurality of detector modules greater than the number of anti-scatter modules, each said detector module including a second reference surface and one or more detectors, fixed relative to said second reference surface, for detecting X-rays generated by said source; and, base support means, adapted to be secured to said X-ray system, for supporting said detector and anti-scatter modules and having a base reference surface and including positioning means for properly positioning and fixing each of said modules to said base support means so that the reference surface of each of said modules is in mutually confronting relationship with the base reference surface and so that the detector module and anti-scatter module are accurately positioned with respect to said source when said modules and base support means are secured to said X-ray system.

28. A modular arrangement for an X-ray detector assembly carried opposite a source of X-rays on a rotating disk of a tomographic system, said arrangement comprising:

(A) a spine having a substantially flat reference surface and a plurality of spine reference holes in and substantially normal to said spine reference surface;

(B) a plurality of anti-scatter modules each attached to said spine at least at two locations, each anti-scatter module having:
 (a) means defining a substantially flat anti-scatter module reference surface for contacting said spine reference surface;
 (b) a round, anti-scatter module reference hole normal to said anti-scatter module reference surface thereby defining one of said at least two locations;
 (c) an anti-scatter module reference slot normal to said anti-scatter module reference surface, and having its elongated dimension substantially in alignment with said anti-scatter module reference hole, thereby defining another of said at least two locations; and (d) a plurality of anti-scatter plates, accurately located and oriented with respect to said anti-scatter module reference hole, reference slot and reference surface;

(C) a plurality of detector modules attached to said spine, each detector module having:
  (a) means defining a substantially flat detector module reference surface for contacting said spine reference surface;
  (b) a round, detector module reference hole normal to said detector module reference surface;
  (c) a detector module reference slot normal to said detector module reference surface, said detector module reference slot having its elongated dimension substantially in alignment with said detector module reference hole; and
  (d) a plurality of X-ray detectors, accurately located and oriented with respect to said detector module reference hole, detector module reference slot and detector module reference surface;

(D) spine mounting means for mounting said spine to said tomographic system;

(E) a plurality of dowel pins;

(F) the location on said spine reference surface of each of said anti-scatter and detector modules being determined by one of said dowel pins positioned respectively in its respective reference hole and a corresponding spine reference hole; and (G) the alignment of each of said anti-scatter and detector modules being determined by one of said dowel pins positioned respectively in its respective reference slot and a corresponding spine reference hole.

29. An arrangement as in claim 28, wherein the locations of both an anti-scatter module and a first detector module are determined by the same dowel pin and spine reference hole.

30. An arrangement as in claim 29, wherein said plurality of spine reference holes comprises:

a first plurality of primary reference holes, accurately located with respect to each other;

a second plurality of secondary reference holes associated with and accurately located with respect to each respective reference hole, the location of each of said anti-scatter modules being determined by one of said dowel pins in a primary reference hole; and the alignment of each of said anti-scatter modules being determined by one of said dowel pins in a secondary reference hole.

31. An arrangement as in claim 29, wherein the dowel pin and spine reference hole that determine the location of a second detector module also determine the location of an anti-scatter module in alignment with said first and second detector modules.

32. An arrangement as in claim 31, wherein the dowel pin that determines the location of a third detector module, that is positioned between said first and second detector modules, passes through without touching an oversized anti-scatter module reference hole normal to said anti scatter module reference surface.

33. An arrangement as in claim 32, wherein there are more of said detector modules than said anti-scatter modules.

34. An arrangement as in claim 28, wherein said mounting means attaches to opposite ends of said spine and to said disk of said tomographic system.

35. An arrangement as in claim 34, wherein said mounting means comprises first adjusting means for making fine adjustments in the distance between each of said spine ends and said X-ray source.

36. An arrangement as in claim 34, wherein said mounting means comprises second adjusting means for making fine adjustments in the angular rotation of said spine with respect to said X-ray source.

37. In a modular arrangement for an X-ray detector assembly for use with a source of X-rays in an X-ray system when:in at least one detector module and at least one anti-scatter module are mounted in alignment on a substantially flat base reference surface of a base support means adapted to be secured to said X-ray system for supporting said detector and anti-scatter modules, the improvements comprising:

(a) each said anti-scatter module comprising a substantially flat anti-scatter reference surface parallel to and at least partly in contact with said base reference surface; first anti-scatter module positioning means for referencing a first anti-scatter surface location, characterized by the region surrounding an anti-scatter point along said anti-scatter reference surface, to a first location on said base reference surface; and second anti-scatter module positioning means for referencing a second anti-scatter surface location, characterized by the region surrounding an anti-scatter line segment along said anti-scatter reference surface, to a second location on said base reference surface, further wherein said anti-scatter line segment and said anti-scatter point lie substantially in a straight line along said anti-scatter reference surface;

(b) each said detector module comprising a substantially flat detector reference surface parallel to and at least partly in contact with said base reference surface; first detector module positioning means for referencing a first detector surface location, characterized by the region surrounding a detector point along said detector reference surface, to said second location on said base reference surface; and second detector module positioning means for referencing a second detector surface location, characterized by the region surrounding a detector line segment along said detector reference surface, to a third location on said base reference surface, further wherein said detector line segment and said detector point lie substantially in a straight line along said detector reference surface; and, (c) said base reference surface comprising base positioning means adapted to align and mate respectively with said detector module positioning means and said anti-scatter module positioning means for fixing each of said modules to said base support means at said respective first and second anti-scatter and detector module surface locations so that at least a portion of the reference surface of each of said modules is in mutually confronting relationship with the base reference surface and so that the detector module and anti-scatter module are accurately positioned with respect to said source of X-rays when said modules and base support means are secured to said X-ray system.

38. An arrangement according to claim 37, further wherein said first and second detector module positioning means respectively comprise first and second detector module positioning openings extending substantially normal to said detector reference surface, said first and second anti-scatter module positioning means respectively comprise first and second anti-scatter module positioning openings extending substantially normal to said anti-scatter reference surface, and said base positioning means comprises base positioning openings extending normal to said base reference surface, said arrangement further comprising pins for insertion through said openings such that the detector modules and the anti-scatter modules are accurately positioned with respect to each other and with respect to said X-ray source when said modules and base support means are secured to said X-ray system.

39. An arrangement according to claim 38, further wherein each said detector module is adapted to cooperate with an anti-scatter module such that one of said detector module positioning openings is so aligned with one of said anti-scatter module positioning openings as to receive a common one of said pins.

40. An arrangement according to claim 39, further wherein said first and second openings of each of said modules comprise respectively a circular hole for tightly receiving one of said pins and a slot having a width which is narrower than its length, and wherein the length of said slot is aligned with said circular hole, the width of the slot being dimensioned to tightly receive another one of said pins, while the length of the slot accommodates tolerances between said pins.

41. An arrangement according to claim 40 further wherein said common pin passes through a slot of one of said modules and a circular hole of the other of said modules.

* * * * *